United States Patent [19]
Khokhar et al.

[11] Patent Number: 5,132,323
[45] Date of Patent: * Jul. 21, 1992

[54] 1,2-DIAMINOCYCLOHEXANE-PLATINUM COMPLEXES WITH ANTITUMOR ACTIVITY

[75] Inventors: Abdul R. Khokhar; Robert A. Newman; Irwin H. Krakoff, all of Houston, Tex.

[73] Assignee: Board of Regents, The University of Texas System, Austin, Tex.

[*] Notice: The portion of the term of this patent subsequent to Apr. 30, 2008 has been disclaimed.

[21] Appl. No.: 631,013

[22] Filed: Dec. 20, 1990

Related U.S. Application Data

[63] Continuation-in-part of Ser. No. 932,176, Nov. 17, 1986, Pat. No. 5,011,959.

[51] Int. Cl.$^5$ .................. A61K 31/28; A61K 31/70; A61K 31/555
[52] U.S. Cl. ....................... 514/492; 514/23; 514/184
[58] Field of Search .................. 514/23, 184, 492

[56] References Cited

U.S. PATENT DOCUMENTS

| | | | |
|---|---|---|---|
| 4,169,846 | 10/1979 | Kidani et al. | 260/429 |
| 4,256,652 | 3/1981 | Kidani et al. | 260/429 |
| 4,560,781 | 12/1985 | Totani et al. | 556/137 |
| 4,562,275 | 12/1985 | Speer et al. | 556/7 |
| 4,565,884 | 1/1986 | Andrulis, Jr. | 556/137 |
| 4,568,048 | 4/1987 | Totani et al. | 556/137 |
| 4,575,550 | 3/1986 | Totani | 536/121 |
| 4,577,038 | 3/1986 | Totani et al. | 556/137 |
| 4,578,491 | 3/1986 | Amundsen et al. | 556/137 |
| 4,584,316 | 4/1986 | Rosenberg et al. | 514/492 |
| 4,584,392 | 4/1986 | Smith et al. | 556/137 |
| 4,594,418 | 6/1986 | Speer et al. | 554/225 |
| 4,599,352 | 7/1986 | Narayanan et al. | 514/492 |
| 4,614,811 | 9/1986 | Gandolfi | 556/137 |
| 4,617,189 | 10/1986 | Stockel et al. | 424/162 |
| 4,658,047 | 4/1987 | Vishnurajjala | 556/137 |
| 4,659,849 | 4/1987 | Drobnik et al. | 556/137 |
| 4,661,516 | 4/1987 | Brown et al. | 514/492 |
| 4,665,210 | 5/1987 | Bitha et al. | 556/137 |
| 4,670,458 | 6/1987 | Hlavka et al. | 514/492 |
| 4,673,754 | 6/1987 | Smith et al. | 556/137 |
| 4,675,336 | 6/1987 | Bitha et al. | 514/492 |
| 4,680,308 | 7/1987 | Schwartz et al. | 514/492 |
| 4,707,352 | 11/1987 | Stavrianpoulos | 424/1.1 |
| 4,720,504 | 1/1988 | Andrulis, Jr. et al. | 514/492 |
| 4,739,087 | 4/1988 | Speer et al. | 556/137 |

FOREIGN PATENT DOCUMENTS

| | | |
|---|---|---|
| 898614 | 5/1984 | Belgium . |
| 0039272 | 11/1981 | European Pat. Off. . |
| 0098121 | 1/1984 | European Pat. Off. . |
| 0113508 | 7/1984 | European Pat. Off. . |
| 0130482 | 1/1985 | European Pat. Off. . |
| 0136012 | 4/1985 | European Pat. Off. . |
| 30155705 | 9/1985 | European Pat. Off. . |
| 0185225 | 6/1986 | European Pat. Off. . |

OTHER PUBLICATIONS

International Search Report, PCT/U.S. 87/02996, Apr. 27, 1988.
Chem. Abstracts, vol. 107 (25) #229147d (see therein JP87 59,289 (Mar. 14, 1987).
Speer et al. "Antitumor activity of platinum complexes of 1,2-diaminocyclohexane isomers" J. Clin. Hematology and Onocology, vol. 8, No. 2, 44–50 (1978).
Dialog Search Report.
Lexis Search Report, Nov. 17, 1985.
Craciunescu et al. "On the preparation, antitumor and cytotoxic evaluation of some new analogs of the cis-dichloro (1,2-diaminocyclohexane) platinum(II) complex" Eur. J. Med. Chem. Clin. Ther. vol. 19, 353–357 (1984).
Loehrer et al., "Cisplatin", Annals of Int. Med., vol. 100, 704–713 (1984).
Zwelling et al., "Platinum Complexes" in Pharmacologic Principles of Cancer Therapy, Sanders: Philadelphia (1982).
Burchenal et al., "Rationale for Development of Platinum Analogs," Cancer Treatment Reports, vol. 63, Nos. 9–10, Sep.–Oct. 1979, pp. 1493–1497.

*Primary Examiner*—Jerome D. Goldberg
*Attorney, Agent, or Firm*—Arnold White & Durkee

[57] ABSTRACT

The invention relates to a process for the treatment of tumors in animals with water soluble square-planar cis platinum(II) four-coordinate complexes comprising different nonvalent and divalent organic cations. Monovalent cations include galacturonato and N,N-dimethylglycinato and divalent cations include citraconato, 1,1-cyclobutanedicarboxylato, 1,1-cyclopropanedicarboxylato and Z-iminodiacetato where Z is bound to the nitrogen and is ethyl, propyl, isopropyl, n-butyl, secbutyl, ter-butyl, n-amyl, isoamyl or —OH. The treatment of animals comprises administering to the animals a pharmaceutical composition comprising a platinum complex of the composition described.

4 Claims, No Drawings

1,2-DIAMINOCYCLOHEXANE-PLATINUM COMPLEXES WITH ANTITUMOR ACTIVITY

This is a continuation-in-part of U.S. patent application Ser. No. 06/932,176 filed Nov. 17, 1986, issued as U.S. Pat. No. 5,011,959.

BACKGROUND OF THE INVENTION

This invention relates to a process for treating tumors in animals using newly synthesized platinum complexes.

Cis-platinum (CDDP) is a highly effective drug in the treatment of several neoplastic diseases in humans (Loehrer et al. (1984) Ann. Int. Med. V. 100, pp 704–713). However, its use is limited by severe systemic toxicity, particularly nephrotoxicity and neurotoxicity (Zwelling et al. Platinum Complexes. In: Pharmacologic principles of cancer treatment (1982) Ed by B. A. Chabner, Saunders, Philadelphia, Pa.). In an attempt to modify the therapeutic index of CDDP, new derivatives have been synthesized during the last decade. However, the development of some promising analogues has been prevented by their low hydrosolubility, which may decrease their potential for clinical use (Burchenal et al. (1979) Cancer Treat. Rep. V. 63, pp. 1493–1497).

In U.S. Pat. No. 4,256,652 are described certain platinum compounds comprising resolved stereoisomers of 1,2-diaminocyclohexane (DACH). The isomers utilized were cis-DACH, trans-RR-DACH and trans-SS-DACH The platinum compounds described therein contained, in addition to a resolved DACH isomer, two hydrophilic platinum ligands such as bromide, iodide, nitrate, bromoacetate, sulfate or glucuronate. The platinum compounds comprising the trans-RR-DACH were described as often more therapeutically effective than those bearing cis-DACH.

In European Patent Application No. 184107104.6 (Public. No. 0130482, Brown et al., published Jan. 1, 1985) many platinum complexes are described. The platinum complexes described therein comprised DACH and carboxylate ligands including:
N-(2-hydroxyethyl)-iminodiacetato
N-(2-acetamido)-diacetato
N-methyliminodiacetato
trans-1,2-cylclopropanedicarboxylato
trans-1,2cyclobutanedicarboxylato
glycinato
isocitratomonoethylester
D,L-isocitratolactone
ascorbato
D-monosaccharato
D-saccharato-1,4-lactone.

These complexes comprised DACH of an undefined stereochemical structure and, in contrast to the complexes of the present invention, were presumably racemic mixtures of all possible DACH stereoisomers. These complexes are further distinguished from those of the present invention by virtue of their carboxylato ligands, analogous in some cases but different.

Advantages of the compounds of the present invention include:
1) High antitumor activity;
ii) Lowered potential to produce nephrotoxicity;
iii) Lack of cross-resistance in in vitro antitumor cell cultures resistant to cisplatin (i.e., L1210/cisplatin); and
iv) High aqueous solubility.

SUMMARY OF THE INVENTION

The present invention comprises a process for the treatment of animals with water soluble square-planar cis-platinum(II) four-coordinate complexes having the formula:

trans-R,R-DACH Pt(II) $X_2$ or trans-R,R-DACH Pt(II) Y wherein X is a monovalent cation selected from the group consisting of galacturonato and N,N-dimethylglycinato; wherein Y is a divalent cation selected from the group consisting of citraconato, 1,1-cyclobutanedicarboxylato, 1,1-cyclopropanedicarboxylato and Z-iminodiacetato where Z is bound to the nitrogen and is ethyl, propyl, isopropyl, n-butyl, sec-butyl, ter-butyl, n-amyl, isoamyl or OH.

Other water-soluble square-planar cis-platinum(II) four-coordinate complexes useful in the practice of the invention have the formula:

trans-R,R-DACH Pt(II) $X_2$ wherein X is a monovalent cation. Two X substituents are present in the platinum complex. These X substituents are preferably selected from the group consisting of galacturonato and N,N-dimethylglycinato. Both X substituents are usually identical but may be different.

When the water-soluble square-planar cis-platinum(II) four-coordinate complex has the formula:

trans-R,R-DACH Pt(II) Y the Y substituent is preferably a single divalent cation selected from the group consisting of citraconato, 1,1-cyclobutanedicarboxylato, 1,1-cyclopropanedicarboxylato and Z-iminodiacetato where Z is bound to the nitrogen and is ethyl, propyl, isopropyl, n-butyl, sec-butyl, ter-butyl, n-amyl, isoamyl or OH.

In a most preferred embodiment the water-soluble square-planar cis-platinum(II) four-coordinate complexes most useful have the formula:

trans-R,R-DACH Pt(II) Y wherein Y is Z-iminodiacetato where Z is ethyl, propyl, isopropyl, n-butyl, sec-butyl, ter-butyl, n-amyl, isoamyl or OH.

The complexes of the present invention demonstrate marked utility in a process for treating animals having tumors sensitive to these complexes. This process comprises administering to said animals a pharmaceutical composition consisting essentially of a therapeutically anti-tumor effective amount of the water-soluble square-planar cis-platinum(II) four-coordinate complex described above. For this process a pharmaceutical composition comprising a platinum complex of the present invention may be utilized. This pharmaceutical composition is preferably in a unit dosage form suitable for administration to an animal afflicted with tumor cells. The unit dosage comprises a therapeutically antitumor effective amount of the water-soluble square-planar cisplatinum(II) four-coordinate complex The therapeutically antitumor effective amount should usually be between 1 mg/kg and 20 mg/kg but may vary considerably based upon tumor type and the judgement of the attending therapist. Likewise the dosage frequency and duration are variable.

The pharmaceutical composition may be any vehicle suitable for injection, the usual mode of administration. Introduction into the body may be intravenous, intramuscular or intraperitoneally and the dispersing vehicle will be chosen accordingly. Since the complexes are water soluble, suitable diluents include but are not limited to physiological saline, sterile water, and water miscible solvents suitable for injection.

DESCRIPTION OF THE PREFERRED EMBODIMENT

Cis-platin is an important anticancer drug which has the potential to produce life-threatening nephrotoxicity. While new platinum antitumor drugs have been produced which are relatively free from the potential to produce renal injury, many experience significant water solubility problems. The present invention comprises several diaminocyclohexane platinum (DACH-Pt) antitumor complexes which: (1) retain or surpass the antitumor efficacy of cisplatin, (2) are non-cross resistant with cisplatin in a murine leukemia cell line which is specifically resistant to this drug (L1210/cisplatin), (3) are non-nephrotoxic, and (4) are water soluble. These compounds offer distinct advantages as antitumor agents over the use of cisplatin. Table 1 lists the complexes of the present invention.

TABLE 1

| Number | COMPOUNDS OF THE PRESENT INVENTION<br>Compound |
|---|---|
| 1 | N-ethyliminodiacetato(trans-R,R-DACH)Pt(II).H$_2$O |
| 2 | N-propyliminodiacetato(trans-R,R-DACH)Pt(II).2H$_2$O |
| 3 | N-butyliminodiacetato(trans-R,R-DACH)Pt(II).2H$_2$O |
| 4 | N-amyliminodiacetato(trans-R,R-DACH)Pt(II).H$_2$O |
| 5 | N-isopropyliminodiacetato(trans-R,R-DACH)Pt(II).2H$_2$O |
| 6 | N-isoamyliminodiacetato(trans-R,R-DACH)Pt(II) |
| 7 | N-sec-butyliminodiacetato(trans-R,R-DACH)Pt(II).2H$_2$O |
| 8 | N-ter-butyliminodiacetato(trans-R,R-DACH)Pt(II).3H$_2$O |
| 9 | N-hydroxyliminodiacetato(trans-R,R-DACH)Pt(II).2H$_2$O |
| 10 | Citraconato(trans-R,R-DACH)Pt(II).1H$_2$O |
| 11 | 1,1-Cyclobutanedicarboxylato(trans-R,R-DACH)Pt(II).1½H$_2$O |
| 12 | 1,1-Cyclobutanedicarboxylato(trans-S,S-DACH)Pt(II).2H$_2$O |
| 13 | 1,1-Cyclobutanedicarboxylato(cis-DACH)Pt(II).1½H$_2$O |
| 14 | 1,1-Cyclopropanedicarboxylato(trans-R,R-DACH)Pt(II).H$_2$O |
| 15 | Cis-bis-galacturonato(trans-R,R-DACH)Pt(II).2H$_2$O |
| 16 | Cis-bis-N,N-dimethylglycinato(trans-R,R-DACH)Pt(II).2H$_2$O |

DACH = 1,2-diaminocyclohexane

The following examples are presented to describe preferred embodiments and utilities of the present invention and are not meant to limit the present invention unless otherwise stated in the claims appended hereto.

EXAMPLE 1

Cis-bis-dichloro(trans-R,R-DACH)platinum(II)

To an aqueous filtered solution of 16.6 g K$_2$PtCl$_4$ (0.04 mole in 250 ml of water) 4.56 g (8.4 mmole) of trans-R,R-DACH was added. The reaction mixture was stirred at room temperature for 6-8 hours. A yellow solid was precipitated, filtered, washed with water, methanol and finally with acetone. The final product was dried under vacuum. Yield=56%.

Cis-bis-dichloro(trans-S,S-DACH)platinum(II) and cis-bis-dichloro(cis-DACH)platinum(II) were prepared in an analogous manner using stoichiometric amounts (ca. 1 mmole) of K$_2$PtCl$_4$ and the respective DACH isomers, i.e., trans-S,S and cis-.

EXAMPLE 2

Sulfato (DACH)platinum(II).H$_2$O

Dichloro (DACH)platinum(II), (DACH being trans-R,R-, trans-S,S- or cis isomer), (1.0 g; 2.6 mmole) was suspended ion water (20 ml), and a solution of Ag$_2$SO$_4$ (0.75 g; 2.4 mmole) in water (150 ml) was added. The reaction mixture was stirred at room temperature for 24 hours in the dark. The precipitated AgCl was filtered off, and the yellow filtrate was evaporated to dryness at 45°-50° C. under reduced pressure using a rotary evaporator. A yellow product was obtained and dried over P$_2$O$_5$ under vacuum. Yield: 90%.

EXAMPLE 3

N-ethyliminodiacetato(trans-R,R-DACH)platinum (II) H$_2$O

Sulfato (trans-R,R-DACH)platinum (II) H$_2$O (0.423 g) was dissolved in water (25 ml) and an aqueous solution of barium ethyliminodiacetate (0.332 g) was added thereto. The reaction mixture was stirred for 30 minutes at room temperature. BaSO$_4$ precipitate was filtered and filtrate was evaporated to dryness at 40°-45° C. under reduced pressure using a rotary evaporator. A cream-colored solid was obtained which was finally purified from n-propanol. The product was dried over P$_2$O$_5$ in vacuo. Yield: 56%.

The analytical data for the product are set forth in Table 2. Other complexes of the invention, i.e., N-propyliminodiacetato, N-butyliminodiacetato, N-amyliminodiacetato, N-isopropyliminodiacetato, N-isoamyliminodiacetato, N-sec-butyliminodiacetato, N-ter butyliminodiacetato and N-hydroxyliminodiacetato were prepared in an analogous manner to the above-mentioned method using stoichiometric amounts (ca 1 mmole) sulfato (trans-R,R-DACH)-platinum(II).H$_2$O and the respective barium salts of N-substituted iminodiacetic acids.

EXAMPLE 4

Citraconato (trans-R,R-DACH)Pt(II).2H$_2$O

Sulfato(trans-R,R-DACH)platinum(II) H$_2$O (0.423 g) was dissolved in water (20 ml) and a solution of barium citraconate prepared in situ (citraconic acid (0.13 g) and Ba(OH)$_2$.8H$_2$O (0.3 g) in H$_2$O) was added thereto. The reaction mixture was stirred for 30 minutes at room temperature. Barium sulfate precipitate was filtered and the filtrate was evaporated to dryness at 40°–45° C. under reduced pressure using a rotary evaporator. A cream colored product was obtained which was further dried over $P_2O_5$ in vacuo.

The analytical data for these complexes are set forth in Table 2.

EXAMPLE 5

1,1-Cyclobutanedicarboxylato (trans-R,R-DACH)platinum(II)

Sulfato(trans-R,R-DACH)platinum(II).$H_2O$ (0.423 g) was dissolved in water (100 ml) and barium 1,1-cyclobutanedicarboxylate prepared in situ [1,1-cyclobutanedicarboxylic acid (0.13 g) and $Ba(OH)_2.8-H_2O$ (0.3 g) in (200 ml) water was added thereto. The reaction mixture was stirred for 30 minutes at room temperature. Barium sulfate was filtered and the filtrate was evaporated to dryness at 40°–45° C. under reduced pressure using a rotary evaporator. Solid was obtained which was purified from water. The final product was dried in vacuo.

1,1-Cyclobutanedicarboxylato(trans-S,S-DACH)-platinum(II) and 1,1-cyclobutanedicarboxylato(cis-DACH) platinum(II) were prepared in an analogous manner to the above mentioned method but using trans-S,S-DACH and cis-DACH ligands.

The analytical data for the products are set forth in Table 2.

TABLE 2

| Compound No. | ANALYTICAL DATA | | | | | |
|---|---|---|---|---|---|---|
| | % Observed | | | % Calculated | | |
| | C | H | N | C | H | N |
| 1 | 29.99 | 5.44 | 8.02 | 29.63 | 5.21 | 8.64 |
| 2 | 29.85 | 5.12 | 7.61 | 30.11 | 5.64 | 8.10 |
| 3 | 31.52 | 5.72 | 7.55 | 31.58 | 5.87 | 7.89 |
| 4 | 33.17 | 5.71 | 7.47 | 32.96 | 6.08 | 7.69 |
| 5 | 30.08 | 5.46 | 7.65 | 30.11 | 5.64 | 8.10 |
| 6 | 32.85 | 5.62 | 6.42 | 32.96 | 6.08 | 7.64 |
| 7 | 31.31 | 5.49 | 7.42 | 31.58 | 5.87 | 7.63 |
| 8 | 31.09 | 5.81 | 7.25 | 30.54 | 6.04 | 7.63 |
| 9 | 23.77 | 4.38 | 7.76 | 23.53 | 4.94 | 8.23 |
| 10 | 28.95 | 4.55 | 6.21 | 29.0 | 4.39 | 6.15 |
| 11 | 29.83 | 4.80 | 5.74 | 30.1 | 4.81 | 5.85 |
| 12 | 29.44 | 4.49 | 5.19 | 29.56 | 4.92 | 5.74 |
| 13 | 30.13 | 4.32 | 5.55 | 30.13 | 4.81 | 5.55 |
| 14 | 28.98 | 4.51 | 6.03 | 29.00 | 4.61 | 6.15 |
| 15 | 29.34 | 5.07 | 3.66 | 29.53 | 4.65 | 3.83 |
| 16 | 30.96 | 6.26 | 10.15 | 30.60 | 6.20 | 10.20 |

EXAMPLE 6

The in Vitro Antitumor Activities of the Complexes of the Invention

Wild-type L1210 leukemic cells were grown as a suspension culture in McCoy's 5A medium supplemented with 10% horse serum, glutamine, streptomycin and penicillin at 37° C., 95% relative humidity and 5% $CO_2$. Four ml of cell suspension ($10^5$ cells/ml) were added to culture tubes and the appropriate amount of drug was added (to yield 0.01, 0.1, 1 or 10 µg/ml final concentration) to the culture tubes. After 72 hours of incubation, the cell concentration in control and experimental cultures were determined with the aid of the Coulter counter model ZB/ and the percent of growth inhibition calculated. The in vitro cytotoxicities of platinum complexes of the present invention are shown in Table 3.

TABLE 3

| IN VITRO CYTOTOXICITY | |
|---|---|
| Compound No. | $ID_{50}(\mu g/ml)$ |
| 1 | 0.73 |
| 2 | 0.75 |
| 3 | 0.74 |
| 4 | 3.00 |
| 5 | 0.85 |
| 6 | N.D. |
| 7 | 0.65 |
| 8 | N.D. |
| 9 | 0.76 |
| 10 | 5.00 |
| 11 | N.D. |
| 12 | 1.65 |
| 13 | 3.30 |
| 14 | 0.66 |
| 15 | 0.90 |
| 16 | 3.5 |

EXAMPLE 7

In Vivo Antitumor Therapy Against L1210

$BDF_1$ mice were inoculated intraperitoneally with $10^6$ L1210 cells. About 24 hours after inoculation (day 1), the mice were injected intraperitoneally with varying doses of complexes of the present invention. Six mice were used for each dosage level with an equal number of mice inoculated with $10^6$ L1210 cells being left untreated as controls. The results [% T/C = (survival time of treated animals/survival time of control animals) × 100] are set forth below. Long-term survival signifies that animals were alive 30 days after tumor inoculation. These results are set forth in Table 4.

TABLE 4

| IN VIVO ANTITUMOR ACTIVITIES | | | | |
|---|---|---|---|---|
| Compound No. | Optimal Dose(mg/kg) | Days of Administration | % T/C | Long-term Survivors |
| 1 | 50 | 1 | 125 | — |
| | 12.5 | 1,5,9 | 324 | 1/6 |
| | 3.15 | 1–9 | 434 | 4/6 |
| 2 | 56 | 1 | 129 | — |
| 3 | 12.5 | 1 | 147 | — |
| | 12.5 | 1,5,9 | 318 | 2/6 |
| 4 | 50 | 1 | 158 | — |
| | 25 | 1,5,9 | 227 | 2/6 |
| 5 | 50 | 1 | 155 | — |
| | 12.5 | 1,5,9 | 324 | 1/6 |
| 6 | 50 | 1 | 145 | — |
| | 12.5 | 1,5,9 | 150 | — |
| 7 | 6.25 | 1,5,9 | 282 | 2/6 |
| 8 | 6.25 | 1,5,9 | 271 | 1/6 |
| 9 | 50 | 1 | 156 | — |
| | 25 | 1,5,9 | 265 | — |
| 10 | 25 | 1,5,9 | 200 | — |
| 11 | 50 | 1 | 147 | — |
| | 12.5 | 1,5,9 | 140 | — |
| | 6.25 | 1–9 | 398 | 3/6 |
| 12 | 12.5 | 1–9 | 120 | — |
| 13 | 12.5 | 1–9 | 253 | 1/6 |
| 15 | 12.5 | 1,5,9 | 238 | — |

EXAMPLE 8

In Vivo Renal and Hematological Toxicity of Dach-Pt(II) Compounds $CD_1$ albino mice were administered a single intraperitoneal injection of the $LD_{50}$ dose of each compound using 5 mice in each group. Five days later each mouse was bled under anesthesia from the axillary vessel. Blood urea nitrogen (BUN) and leucopenia were assessed for each sample. Results are shown in Table 5 and presented as ±S.D.

TABLE 5
RENAL AND HEMATOLOGICAL TOXICITIES OF DACH-Pt (II) COMPOUNDS

| No. | Compound | $LD_{50}$ (mg/kg.ip) | Survivors on d.5 | Body Weight d.5 (% of day 0) | BUN d.5[a] (with $LD_{50}$) | WBC d.5 (XL109/1) |
|---|---|---|---|---|---|---|
| 1 | R,R-EIDA | 58 | 5/5 | 105 | 23.5 ± 3.8 | 2.3 ± 0.93 |
|  | S,S-EIDA | 95 | 5/5 | 100 | 20.4 ± 5.5 | 2.63 ± 0.96 |
|  | Cis-EIDA | 140 | 3/5 | 77 | 36.0 ± 7.0 | 3.25 ± 1.01 |
| 11 | R,R-CBDCA | 280 | 5/5 | 121 | 28.3 ± 2.9 | 3.44 ± 1.55 |
| 12 | S,S-CBDCA | 230 | 3/5 | 114 | 34.0 ± 2.6 | 3.42 ± 1.93 |
| 13 | Cis-CBDCA | 215 | 5/5 | 82 | 17.0 ± 8.1 | 1.13 ± 0.28 |
|  | Carboplatin | 105 | 5/5 | 95 | 22.8 ± 8.6 | 1.51 ± 1.01 |
|  | Cisplatin | 12 | 4/5 | 86 | 72.5 ± 52.4 | 3.47 ± 1.83 |
|  | Saline |  | 5/5 | 121 | 20.8 ± 5.2 | 3.21 ± 1.4 |

[a]$CD_1$ Albino mice were administered a single i.p. injection of the $LD_{50}$ dose of each compound (5 mice/cmpd) and bled under anesthesia from the axillary vessel 5 days later for blood urea nitrogen (BUN) measurement and assessment of leucopenia. Results as presented as mean ± S.D.
EIDA - N-Ethyliminodiacetato (DACH) Pt (II)
CBDCA - 1,1-Cyclobutanedicarboxylato (DACH) Pt (II)
Antitumor efficacy of the DACH Pt(II) compounds is summarized in Table 2.

EXAMPLE 9
In Vivo Antitumor Efficacy of Dach-Pt(II) Compounds $BDF_1$ mice were inoculated intraperitoneally with $10^5$ L1210 cells, 0.5 ml of 10% tumor brei or $10^6$ M5076 cells using 5 animals in each group. Drug was administered three times daily on days 1, 5 and 9, except that the group infected with M5076 cells was also injected on day 13. % T/C represents mean survival time treated/mean survival time of the control times 100. Results are shown in Table 6.

As indicated in the table, the N-ethyliminodiacetato trans R,R-DACH Pt(II) (compound 1) increased survival time over controls for mice inoculated with L1210 cells by 324%. The 1,1-cyclobutanedicarboxylato DACH PT(II) (compound 11) increased survival time over controls for mice inoculated with L1210, B16 or M5076 cells by 118%, 104% and 220% respectively. There was one long term survivor from the M5076 inoculated group. The 1,1-cyclobutanedicarboxylato trans S,S-DACH Pt(II) (compound 12) increased survival time over controls for mice inoculated with L1210, B16 or M5076 cells by 176%, 104% and 231% respectively. The 1,1-cyclobutanedicarboxylato DACH Pt(II) (compound 13) increased survival time over controls for mice inoculated with L1210, B16 or M5076 cells by 150%, 200% and 400% respectively. There was 1/5 long term survivor from B16 inoculation and 5/5 survivors from M5076 inoculation.

EXAMPLE 10

TABLE 6
IN VIVO ANTITUMOR EFFICACY OF DACH-Pt(II) COMPOUNDS

| | | L1210/cisplatin[a] | | B16[b] | | | M5076[c] | | |
|---|---|---|---|---|---|---|---|---|---|
| No. | Compound | Opt. dose (mg/kg) | % T/C[d] | Opt. dose (mg/kg) | % T/C | LTS[e] | Opt. dose (mg/kg) | % T/C | LTS |
| 1 | R,R-EIDA | 12.5 | 324 | | | | | | |
|  | S,S-EIDA | 25 | 344 | | | | | | |
|  | Cis-EIDA | 75 | 262 | | | | | | |
| 11 | R,R-CBDCA | 150 | 118 | 50 | 104 | | 50 | 220 | 1/5 |
| 12 | S,S-CBCA | 100 | 176 | 50 | 104 | | 50 | 231 | 1/5 |
| 13 | Cis-CBDCA | 150 | 150 | 100 | 200 | 1/5 | 100 | 400 | 5/5 |
|  | Cisplatin | 5 | 94 | 3 | 139 | | 3 | 200 | |
|  | Carboplatin | 90 | 121 | | | | 40 | 150 | |

[a]$BDF_1$ mice were inoculated i.p. with $10^5$ L1210 cells. Mice received 3 i.p. drug injections days 1, 5, and 9.
[b]$BDF_1$ mice inoculated i.p. with B16 melanoma 0.5 ml of 10% tumor brei and treated on days 1, 5, and 9 (i.p.).
[c]$BDF_1$ mice were inoculated i.p. with $10^6$ M5076 cells. Mice received 4 i.p. drug injections on days 1, 5, 9 and 13.
[d]% T/C = (Mean Survival Time treated/Mean Survival Time control) × 100.
[e]LTS animals alive 60 days after inoculation of L1210/0 and B16 and 90 days after inoculation B5076.
EIDA - N-Ethyliminodiacetato (DACH) Pt (II)
CBDCA - 1,1-Cyclobutanedicarboxylato (DACH) Pt (II)

Structural Formulas

Structural formulas for compounds of the present invention described in Tables 1 and 2 and elsewhere herein are shown in Table 7 (not including water of hydration, which is not critical).

TABLE 7
STRUCTURAL FORMULAS OF THE WATER-SOLUBLE SQUARE-PLANAR CIS-PLATINUM FOUR-COORDINATE COMPLEXES OF THE PRESENT INVENTION

| COMPOUND NUMBER | NAME | STRUCTURE |
|---|---|---|
| 1. | N-ethyliminodiacetato(trans-R,R-DACH)Pt(II).H$_2$O: | 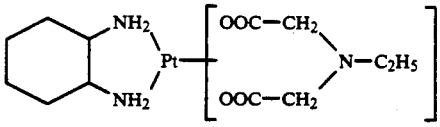<br>also described in trans-R,R-DACH Pt(II)Y, where Y is the divalent cation Z-iminoiacetato and Z is ethyl bound to the nitrogen. |
| 2. | N-propyliminodiacetato(trans R,R-DACH)Pt(II).2H$_2$O | 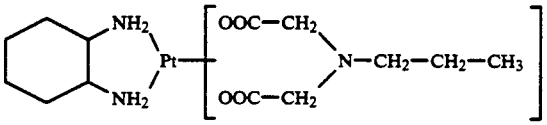<br>also described as trans-R,R-DACH Pt(II)Y where Y is the divalent cation Z-iminodiacetato and Z is propyl bound to the nitrogen. |
| 3. | N-butyliminodiacetato(trans-R,R-DACH)Pt(II).2H$_2$O | 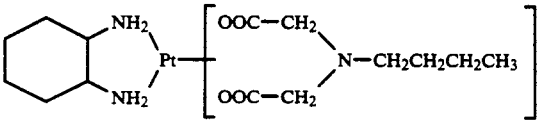 |
| 4. | N-amyliminodiacetato(trans-R,R-DACH)Pt(II).H$_2$O | 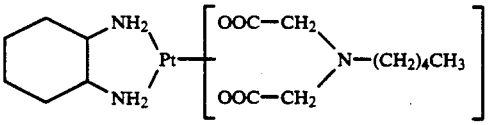<br>also described as compound 1-3 but with Z being amyl. |
| 5. | N-isopropyliminodiacetato(trans-R,R-DACH)Pt(II).2H$_2$O | 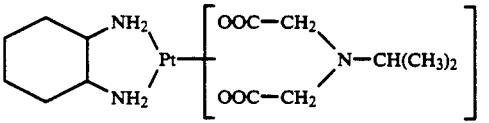<br>also described as compounds 1-4 but with Z being isopropyl. |
| 6. | N-isoamyiminodiacetato(trans-R,R-DACH)Pt(II) | 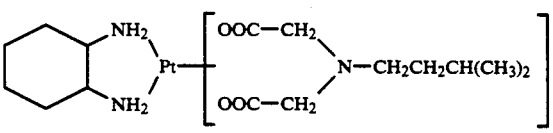<br>also described as compounds 1-5 but with Z being isoamyl. |
| 7. | N-sec-butyliminodiacetato(trans-R,R-DACH)Pt(II).2H$_2$O | 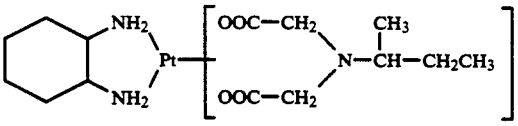<br>also described as compounds 1-6 but with Z being sec butyl. |
| 8. | N-t-butyliminodiacetato(trans-R,R-DACH)Pt(II).3H$_2$O | 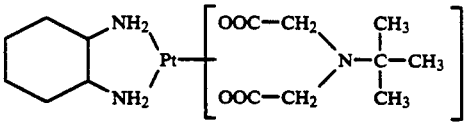<br>also described as compounds 1-7 but with Z being tertiary butyl. |
| 9. | N-hydroxyiminodiacetato(trans-R,R-DACH)Pt(II).2H$_2$O | 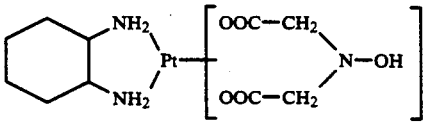<br>also described as compounds 1-8 but with Z being hydroxy. |

TABLE 7-continued
STRUCTURAL FORMULAS OF THE WATER-SOLUBLE SQUARE-PLANAR CIS-PLATINUM FOUR-COORDINATE COMPLEXES OF THE PRESENT INVENTION

| COMPOUND NUMBER | NAME | STRUCTURE |
|---|---|---|
| 10. | Citraconato(trans-R,R-DACH) Pt(II).H$_2$O | 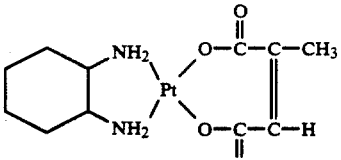 also described as trans-R,R-DACH Pt(II)Y where Y is the divalent cation citraconato. |
| 11. | 1,1-cyclobutanedicarboxylato(trans-R,R-DACH) Pt(II).1½ H$_2$O. | 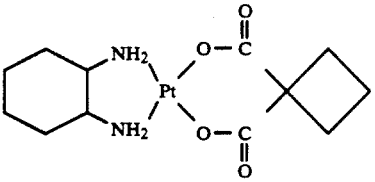 also described as compound 10 but with Y being the divalent cation 1,1 cyclobutanedicarboxylato. |
| 12. | Same as compound 11 but with (trans-S,S-DACH) in place of (trans-R,R-DACH). | |
| 13. | Same as compound 11 but with (cis-DACH) in place of (trans-R,R-DACH). | |
| 14. | 1,1-cyclopropanedicarboxylato(trans-R,R-DACH) Pt(II).H$_2$O | 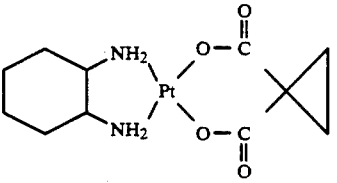 also described as compound 10 but with Y being the divalent cation 1,1 cyclopropanedicarboxylato. |
| 15. | Cis-bis-galacturonato(trans-R,R-DACH) Pt(II)2H$_2$O | 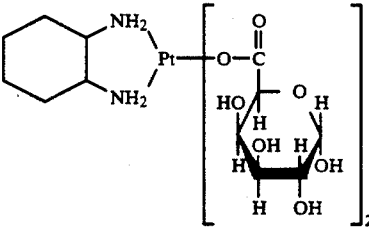 also described as compound 16 but with Z being the monovalent cation galacturonato. |
| 16. | Cis-bis-N-N-Dimethylglycinato(trans-R,R-DACH) Pt(II)2H$_2$O | 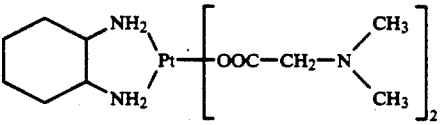 also described as compound 16 but with X being the monovalent cation N,N-dimethylglycinato. |

Changes may be made in the elements and reagents or in the steps or the sequence of steps of the methods described herein without departing from the content and scope of the invention as defined in the following claims.

What is claimed is:

1. A process for treating an animal having a tumor sensitive to a platinum complex, the process comprising administering by injection to said animal a pharmaceutical composition consisting essentially of a therapeutic anti-tumor effective amount of a water-soluble square-planar cis-platinum(II) four-coordinate complex having the formula:

trans-R,R-DACH Pt(II) X$_2$ or trans-R,R-DACH Pt(II) Y wherein X is a monovalent cation selected from the group consisting of galacturonato and N,N-dimethylglycinato; wherein Y is a divalent cation selected from the group consisting of citraconato, 1,1-cyclobutanedicarboxylato, 1,1-cyclopropanedicarboxylato and Z-iminodiacetato where Z is bound to the nitrogen and is ethyl, propyl, isopropyl, n-butyl, sec-butyl, ter-butyl, n-amyl, isoamyl or OH.

2. A process for treating an animal having a tumor sensitive to a platinum complex, the process comprising administering by injection to said animal a pharmaceutical composition consisting essentially of a therapeutically anti-tumor effective amount of a water-soluble square-planar cis-platinum(II) four-coordinate complex having the formula:

trans-R,R-DACH Pt(II) $X_2$ wherein X is a monovalent cation selected from the group consisting of galacturonato and N,N-dimethylglycinato.

3. A process for treating an animal having a tumor sensitive to a platinum complex, the process comprising administering by injection to said animal a pharmaceutical composition consisting essentially of a therapeutically anti-tumor effective amount of a water-soluble square-planar cis-platinum(II) four-coordinate complex having the formula:

trans-R,R-DACH Pt(II) Y wherein Y is a divalent cation selected from the group consisting of citraconato, 1,1-cyclobutanedicarboxylato, 1,1-cyclopropanedicarboxylato and Z-iminodiacetato where Z is bound to the nitrogen and is ethyl, propyl, isopropyl, n-butyl, sec-butyl, ter-butyl, n-amyl, isoamyl or OH.

4. A process for treating an animal having a tumor sensitive to a platinum complex, the process comprising administering by injection to said animal a pharmaceutical composition consisting essentially of a therapeutically anti-tumor effective amount of a water-soluble square-planar cis-platinum(II) four-coordinate complex having the formula:

trans-R,R-DACH Pt(II) Y wherein Y is Z-iminodiacetato where Z is bound to the nitrogen and is ethyl, propyl, isopropyl, n-butyl, sec-butyl, ter-butyl, n-amyl, isoamyl or OH.

* * * * *